United States Patent [19]

Regan et al.

[11] 4,016,089

[45] Apr. 5, 1977

[54] DENTURE CLEANING CONCENTRATE

[76] Inventors: Glen B. Regan; Barrier F. Regan, both of 727 Shasts St., Redwood City, Calif. 94063

[22] Filed: Nov. 11, 1974

[21] Appl. No.: 522,328

[52] U.S. Cl. .............................. 252/106; 252/136; 252/139; 252/142; 252/143; 252/144; 252/547

[51] Int. Cl.$^2$ ..................... C11D 1/62; C11D 3/40; C11D 3/48

[58] Field of Search .......... 252/106, 136, 142, 408, 252/547, 108, 102

[56] References Cited

UNITED STATES PATENTS

| | | | |
|---|---|---|---|
| 2,994,664 | 8/1961 | Wachter | 257/87 |
| 3,042,621 | 7/1962 | Kirschenbauer | 252/99 |
| 3,223,643 | 12/1965 | Law | 252/106 |
| 3,243,377 | 3/1966 | Stolar et al. | 252/95 |
| 3,268,455 | 8/1966 | Bryce et al. | 252/142 |
| 3,355,392 | 11/1967 | Cantor et al. | 252/99 |
| 3,634,233 | 1/1972 | Hiltz | 252/3 |
| 3,733,277 | 5/1973 | Wooden et al. | 252/106 |
| 3,785,986 | 1/1974 | Lauster | 252/136 |
| 3,822,212 | 7/1974 | Bryant et al. | 252/136 |
| 3,899,437 | 8/1975 | Regan et al. | 252/106 |

OTHER PUBLICATIONS

The Condensed Chem. Dictionary, 7th Ed., Reinhold Publishing Corp., New York, p. 503.
The Chemical Formulary, Rheinhold Publishing Co., N. Y., 1966, p. 138 (7th Ed.).

Primary Examiner—P. E. Willis, Jr.

[57] ABSTRACT

A denture cleaning concentrate containing orthophosphoric acid, nonionic detergent, a quaternary ammonium germicide and an indicator which undergoes a color change in the pH range 4 to 4.6 is described.

2 Claims, No Drawings

DENTURE CLEANING CONCENTRATE

BACKGROUND OF THE INVENTION

In the past a number of denture cleaning solutions and denture cleaning concentrates in either solid or liquid form which are added to water to form denture cleaning solutions have been available. The usual practice of the consumer is to fill a glass or similar receptacle with the denture cleaning solution or with a mixture of water and denture cleaning concentrate and immerse the denture to be cleaned in the solution. The solution is ordinarily used for a period of some days before it is disposed of and a new solution provided. It is common for the solution either to be discarded while it still retains effective cleaning activity or to be used after its activity has been exhausted. In the first case, the consumer is wasting useful material and in the second, he does not get the cleaning action which he desires. A denture cleaning composition which would permit the consumer to avoid waste and to avoid relying on a cleaning solution whose activity was spent would have enhanced consumer value.

SUMMARY OF THE INVENTION

Pursuant to the present invention, a denture cleaning concentrate is provided for consumers which concentrate contains orthophosphoric acid, a nonionic detergent, a quaternary ammonium germicide and an internal chemical indicator which undergoes a distinctive change in color when at about pH 4.5. It has been determined that when a dispersion of the concentrate in water is used in denture cleaning until the pH of the diluted concentrate reaches about 4.5 the solution becomes incapable of removing calculus deposits from the denture. Accordingly, the consumer may prepare a solution of the concentrate in water and use it in confidence that its cleaning action is unimpaired until the color change is observed. At that time the solution of the concentrate is discarded and a fresh solution is prepared. Thus, the consumer obtains full use of the cleaning composition and avoids continuing its use after its cleaning capability has been exhausted.

DESCRIPTION OF THE PREFERRED EMBODIMENT OF THE INVENTION

An aqueous solution of a denture cleaning concentrate was prepared by dissolving the following materials in the amount shown in water:

| | |
|---|---|
| Orthophosphoric acid | 4.5% by weight |
| Nonyl phenyl polyglycolether (11 ethylene oxide units) | 3.8% by volume |
| Quaternary ammonium germicide BTC 2125M (50% active) | 0.06% by volume |
| Oil of peppermint | 0.072% by volume |
| Brom phenol blue | 0.003% by weight |

In the above concentrate, the phosphoric acid used was food grade 75% orthophosphoric acid. Expressed in volume percent content of this concentration, the acid component amounted to 3.57 volume percent.

The nonyl phenyl polyglycolether in the above composition is representative of a number of water soluble alkyl phenyl polyglycolethers which may be used to function as a nonionic detergent. The alkyl phenyl polyglocolether used in the above composition was obtained from Onyx Oils and Resins Company which sells it under the tradename "Neutronyx 656".

The oil of peppermint is added in small amount only to give the concentrate a pleasant odor. Other essential oils could be added for this purpose or this component could be omitted entirely without loss in the effectiveness of the concentrate.

The brom phenol blue in the above example is an internal chemical indicator which, at pH 3, is yellow and which, at pH 4.6, is blue. Other internal chemical indicators which undergo a distinctive color change at or near about 4.5 could be used instead of the brom phenol blue. For instance, 4,4'-Bis (2-amino-1-Naphthylazo-2,2'-Stilbenedisulfonic Acid which is purple at pH 3 and red at pH 4, or Tetrabromophenolphthalein Ethyl Ester Potassium Salt which is yellow at pH 3 and blue at pH 4.2, or Methyl Orange-Xylene Cyanole which is purple at pH 3.2 and green at pH 4.2 could be used instead of the brom phenol blue but brom phenol blue is preferred because of the brilliance of color at low concentration and the great difference in the colors at low and high pH.

The concentrate is supplied to the consumer in bottles having a capacity of eight ounces or more. The bottles are capped with a cap which, when removed and inverted, becomes a container having a capacity of five cubic centimeters. Directions to the consumer indicate that one capful of the concentrate added to a glass of water (about 250 cc.) provides a suitable denture cleaning solution. Use of 5 cc. of the concentrate in 250 cc. of water gives a solution which has a distinctive yellow color. More of the concentrate may be added to this quantity of water if desired, but at least 5 cc. of the concentrate should be added to 250 cc. of water in order to provide a sufficiently high concentration of the chemical indicator in the resultant denture cleaning solution to enable the consumer to observe the original color and the color change when the activity of the solution has been exhausted without difficulty.

The composition shown in the above example can be varied within reality narrow limits without loss of efficiency.

The orthophosphoric acid content of the concentrate may be varied over the range 4 to 10 percent by weight. At concentrations below 4 percent, the solutions made by adding the concentrate to water lose activity too rapidly. Concentrations above 10 percent by weight are undesirable because of the household hazards that attend the presence of concentrated acid in the medicine cabinet.

Water soluble alkyl phenyl polyglycolethers having 8 to 14 carbon atoms in the alkyl group and 8 to 20 ethylene oxide units forming the polyglycolether chain provide the concentrate with suitable detergency to accomplish its intended purpose. The alkyl phenyl polyglycolether content of the concentrate can be varied in the range about 3.5 to 5 percent by weight. Larger amounts could be introduced into the composition but no benefit is realized which justifies the incremental cost of such larger amounts.

The component of the concentrate exemplified above which is identified as BTC 2125 M is a quaternary ammonium germicide sold under that tradename by Onyx Chemical Company. It consists of equal parts of n-Alkyl dimethyl benzyl ammonium chloride and n-Alkyl dimethyl ethyl benzyl ammonium chloride, the alkyl groups containing mainly 12 to 16 carbon atoms.

Further, quaternary ammonium germicides which are commercially available may be used, such as tri-alkyl benzyl ammonium chloride in which one of the alkyl groups contains at least 10 and preferably 12 to 20 carbon atoms, or trimethyl alkyl ammonium chlorides in which the alkyl group contains 12 to 20 carbon atoms. In general, any quaternary ammonium halide which contains 1 long chain alkyl group, i.e., 12 to 20 carbon atoms and 3 smaller organic radicals such as methyl, ethyl or benzyl, provide the desired germicidal activity to the concentrate. The quantity of quaternary ammonium germicide may be varied in the range about 0.5 to 1.0 percent by weight, larger amounts could be present but would make no beneficial contribution that would off-set the added cost.

As indicated above, internal chemical indicators which undergo a distinctive color change at or close to pH 4.5 may be used in the concentrate and will give consumer visual indication that the activity of the cleaning solution he has prepared has been exhausted. The quantity of chemical indicator introduced into the concentrate must be sufficiently high to give a solution made by mixing one part of the concentrate with 50 parts of water a distinctive color. Amounts in the range about 0.003 to 0.01 are suitable.

The concentrate described in the above example and variations of it within the limits above indicated when diluted with water to form a solution containing one part by volume of concentrate and 50 parts by volume of water give a solution which removes calculus, plaque, tartar and stains from dentures immersed in the solution in a period of 5 to 15 minutes. If the dentures are cleaned in a dentist's office where an ultrasonic agitator is available and the solution and denture are placed in the ultrasonic agitator, cleansing is complete in less than one minute.

When the concentrate is used to prepare a solution in making a 50 to 1 dilution with water, a number of denture cleansings that can be made before the color change which indicates exhaustion of the activity of the solution offurs is ordinarily in the range 5 to 15. This spread appears to be due to variations in the rate which different individuals accumulate deposits on the dentures variations in the frequency with which individuals subject the dentures to cleaning.

I claim:

1. A denture cleaning concentrate consisting essentially of an aqueous solution containing 4 to 10 percent by weight of orthophosphoric acid, 3.5 to 5 percent by weight of a water soluble alkyl phenyl polyglycolether, 0.5 to 1.0 percent by weight of a quaternary ammonium germicide containing one alkyl group of 10 to 20 carbon atoms and three lower organic radicals selected from the group consisting of methyl, ethyl and benzyl and 0.003 to 0.01 percent by weight of a chemical indicator for pH which undergoes a color change at pH about 4.5.

2. Concentrate as defined in claim 1 wherein the chemical indicator is brom phenol blue.

* * * * *